(12) United States Patent
Shastri et al.

(10) Patent No.: US 6,569,654 B2
(45) Date of Patent: May 27, 2003

(54) ELECTROACTIVE MATERIALS FOR STIMULATION OF BIOLOGICAL ACTIVITY OF STEM CELLS

(75) Inventors: Venkatram Shastri, Lower Gwynedd, PA (US); Ivan Martin, Oberwil (CH); Robert Langer, Newton, MA (US); Nahid Rahman, Boston, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/753,407

(22) Filed: Jan. 2, 2001

(65) Prior Publication Data

US 2002/0034796 A1 Mar. 21, 2002

Related U.S. Application Data

(63) Continuation-in-part of application No. 09/156,317, filed on Sep. 18, 1998, now Pat. No. 6,190,893.

(51) Int. Cl.[7] .............................................. C12N 13/00
(52) U.S. Cl. .................................................... 435/173.8
(58) Field of Search ...................................... 435/173.8

(56) References Cited

U.S. PATENT DOCUMENTS 5,843,741 A * 12/1998 Wong et al. ............. 435/173.8
6,095,148 A * 8/2000 Shastri et al. ................ 128/898
6,190,893 B1 * 2/2001 Shastri et al. ............. 435/173.8

FOREIGN PATENT DOCUMENTS

WO   WO 9716545 A1 * 5/1997 ........... C12N/13/00

* cited by examiner

Primary Examiner—Jon P. Weber
(74) Attorney, Agent, or Firm—Choate, Hall & Stewart; Valarie B. Rosen

(57) ABSTRACT

Compositions, methods and systems are provided for the stimulation of biological activities within stem cells by applying electromagnetic stimulation to an electroactive material, wherein the electromagnetic stimulation is coupled to the electromagnetic material. In general the present invention involves attaching or associating the desired cells to or with a surface comprising an electroactive material, and applying electromagnetic radiation directly to the desired area. In preferred embodiments, the stimulation of biological activities within cells results from inducing one or more activities including, but not limited to, gene expression, cell growth, cell differentiation, signal transduction, membrane permeability, cell division, contraction, and cell signaling. In exemplary embodiments, the electroactive materials used in the present invention are either two-dimensional substrates such as thin films having at least one surface of an electroactive material, or in alternative embodiments, the electroactive materials are three-dimensional substrates comprising a matrix having at least one surface of an electroactive material.

61 Claims, 8 Drawing Sheets

FIG. 1
_PRIOR ART_
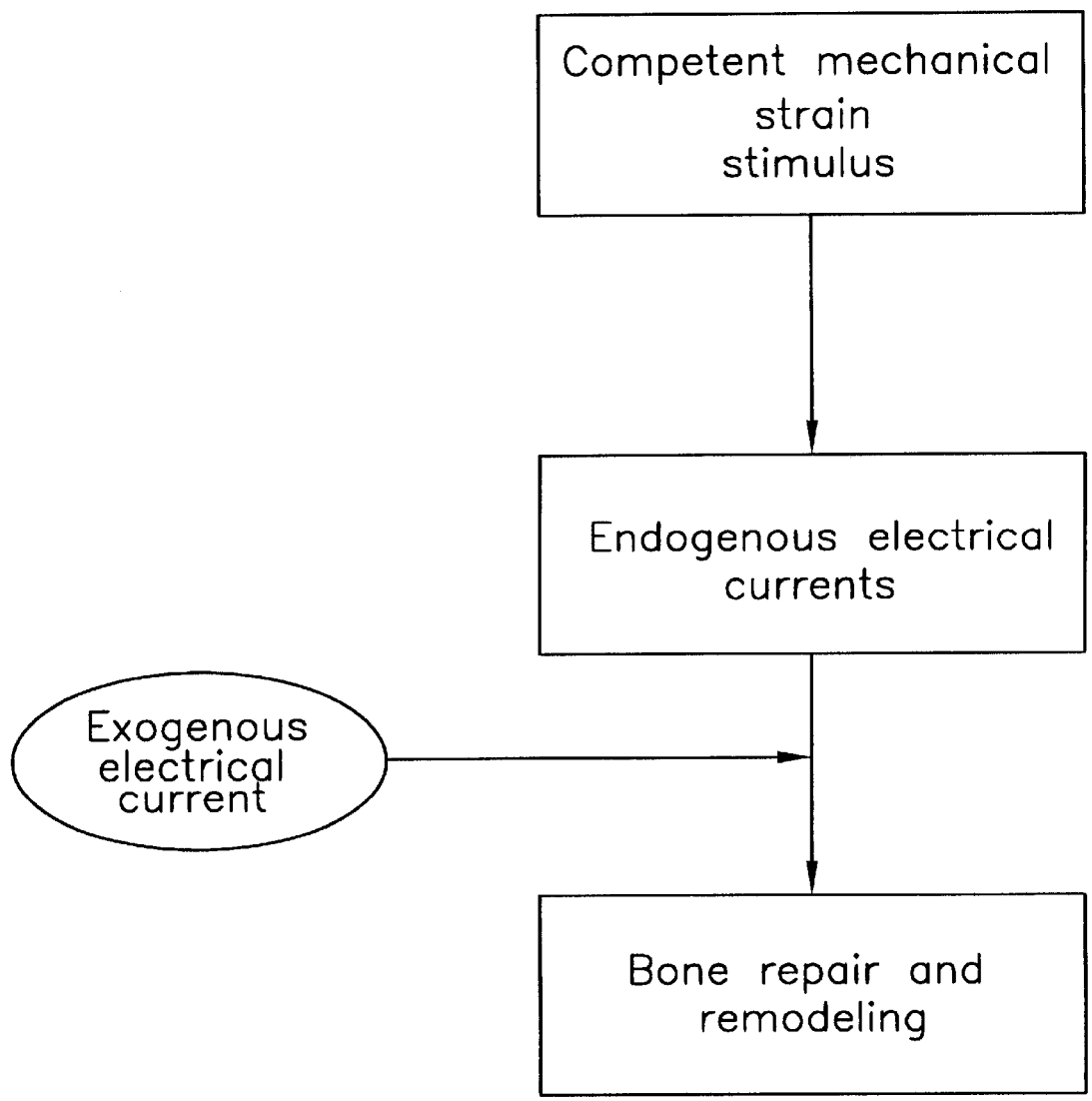

Bipolaron

Bipolaron

ELECTROACTIVE MATERIALS FOR STIMULATION OF BIOLOGICAL ACTIVITY OF STEM CELLS

This application claims the priority of and is a continuation-in-part of U.S. application Ser. No. 09/156,317, filed Sep. 18, 1998, now U.S. Pat. No. 6,190,893, the entire contents of which are incorporated by reference herein.

GOVERNMENT SUPPORT

The government has rights in this invention pursuant to National Science Foundation Grant Number 9525913.

BACKGROUND OF THE INVENTION

Tissue engineering is a field in which the principles of biology, engineering, and materials science are applied to the development of functional substitutes for damaged tissue. (See, Langer, et al., "Tissue Engineering", *Science*, 1993, 260, 920). In general, three different strategies have been adopted for the creation of new tissue: (i) isolated cells or cell substrates, in which only those cells that supply the needed function are replaced; (ii) tissue-inducing substances, such as signal molecules and growth factors, and (iii) cells placed on or within matrices. Researchers have been interested in applying these novel techniques to find replacements for tissues such as ectodermal, endodermal, and mesodermal-derived tissue. In particular, researchers are invested the replacement of tissues in the nervous system, cornea, skin, liver, pancreas, cartilage, bone, and muscle to name a few.

Stem cells have shown tremendous potential for treatment of diseased and damaged tissue. Stem cells are cells that have the potential to both divide for indefinite periods in vitro and to differentiate into more specialized cells. Pluripotent stem cells are a potential source for the development of replacement tissues to treat a variety of medical conditions. For example, nerve stem cells transplanted into the brain may develop into healthy nerves that can counteract the affect of Alzheimer or Parkinson's disease. Tissue engineering applications have long exploited fully differentiated cells seeded onto biocompatible matrices that may be implanted in a wound site to regenerate damaged tissue. The incorporation of stem cells into tissue engineering matrices may increase the therapeutic potential of this technique.

Typically, tissue engineering matrices are designed to either replicate or facilitate restoration of the structural properties of the damaged tissue. The use of electroactive polymers in tissue engineering matrices allows these matrices to replicate or restore the electrical properties of tissue as well. For example, bone is piezoelectric and generates an electrical voltage when mechanically deformed. The electrical activity may mediate remodelling of bone in response to mechanical loading (FIG. 1) (Fukada et al., *J. Phys. Soc. Japan*, 1957, 12, 1158; Becker et al., "The Bioelectric Factors of Controlling Bone Structure", in Bone Biodynamics, R. Bourne, Ed., 1964, Little, Brown and Co.: New York; Bassett et al., *Nature*, 1964, 204, 652). Nerve cells of course work by transmitting electrical signals from the brain to various muscles, and other tissues are responsive to electrical stimulation as well.

Clearly, there remains a need to develop systems and methods whereby biological activities of cells can be stimulated by direct application of electromagnetic stimulation. This would be particularly important in applications to tissue engineering.

SUMMARY OF THE INVENTION

The concept of "tissue engineering" comes into play in the present invention for the development a system in which the biological activities of cells can be stimulated. An interesting class of synthetic polymers explored previously by Langer and co-workers as three-dimensional matrices that can take advantage of these properties are the electrically conducting or electroactive polymers. Based on their ability to respond to electrical or electromagnetic stimuli, they can act as an interface between the external and physiological environments of a connective tissue such as bone, which is capable of undergoing repair and regeneration on exposure to the same stimuli (Shastri et al., "Biomedical Applications of Electroactive Polymers", in *Electrical and Optical Polymer Systems*, D. L. Wise, Wnek, G. E., Trantolo, D. J., Cooper, T. M., Gresser, J. D., Ed., 1998 Marcel Dekker: New York, 1031).

The present invention provides compositions, methods and systems for the stimulation of biological activities within cells by applying electromagnetic stimulation to an electroactive material, wherein the electromagnetic stimulation is coupled to the electroactive material. The present invention provides methods for the stimulation of biological activities within stem cells that involve attaching or associating the stem cells to or with a surface comprising an electroactive material, and applying electromagnetic stimulation directly to the desired area. In preferred embodiments, the stimulation of biological activities within these cells results from inducing one or more activities including, but not limited to, gene expression, cell growth, cell differentiation, signal transduction, membrane permeability, cell division, contraction, and cell signaling. In exemplary embodiments, the electroactive materials are either two-dimensional substrates or three-dimensional substrates comprising a matrix having at least one surface of an electroactive material.

In another aspect, the invention is a method for stimulating one or more biological activities within a cell comprising a composition of stem cells and an electroactive substrate, wherein the electroactive substrateic has at least one surface of electroactive material and the stem cells are attached to the electroactive material or associated with the electroactive substrate. Electromagnetic stimulation coupled to the electroactive material is applied to the composition. The composition is contacted with a mammalian tissue either before or after the step as applying.

In another embodiment, a composition of cells and an electroactive substrate is first provided, wherein the electroactive substrate has at least one surface of electroactive material, and wherein the cells are attached thereto or associated with the electroactive substrate. Subsequently, the electromagnetic stimulation is applied to the composition in vitro, wherein the electromagnetic stimulation is coupled to the electromagnetic material and finally the composition is contacted with mammalian tissue to effect stimulation of cell function. In yet another embodiment, a composition of cells and an electroactive substrate is first provided, wherein the cells are attached thereto or associated with the electroactive substrate. Subsequently, the composition is then contacted with mammalian tissue, and finally the electromagnetic radiation is applied in vivo, wherein the electromagnetic stimulation is coupled to the electroactive material. In particularly preferred embodiments, the electromagnetic stimulation is coupled to the electroactive material by physical contact. In other embodiments, the electromagnetic stimulation is coupled to the electroactive material by electromagnetic induction.

In another aspect of the invention, a system is provided for stimulating one or more biological activities of cells comprising a composition comprising an electroactive substrate, wherein the electroactive substrate has at least one surface of electroactive material, and wherein the electroactive material has attached thereto, or associated therewith, one or more mammalian stem cells. The system further includes apparatus for applying electromagnetic energy at the desired location.

Yet another aspect of the present invention is a two-dimensional stimulant of one or more biological activities of cells comprising one or more films of an electroactive substrate, wherein the one or more films are associated with or attached to one or more mammalian cells at a desired location. A three-dimensional stimulant of one or more biological activities of cells is also provided comprising an electroactive substrate associated with or attached to a matrix and wherein the electroactive substrate is associated with or attached to one or more mammalian cells at a desired location.

Definitions

"Electromagnetic Stimulation": As used herein, the term "electromagnetic stimulation" means any form of electromagnetic energy including, but not limited to, electromagnetic radiation or pulsed electromagnetic field stimulation (PEMF).

"Electroactive material": As used herein, the term "electroactive material" means a material that contains pockets of electron density. This material may be conducting, non-conducting, semiconducting, or piezoelectric, to name a few. For the purposes of the present invention, preferred electroactive materials include electroactive polymers. These electroactive polymers are characterized in that they contain at least a pocket of electron density and are capable of undergoing a phase transition upon subjecting the polymer to an electromagnetic field stimulus.

DESCRIPTION OF THE DRAWING

FIG. 1 depicts a proposed model for regeneration and remodeling of bone in response to electrical stimulation (Modified from Spadaro, A. Bioelectromagnetics, 18:193–202, 1997).

DESCRIPTION OF CERTAIN PREFERRED EMBODIMENTS

Recognizing the need to develop new methods in tissue engineering to directly affect cell activity, growth and/or function, the present invention provides compositions, methods and systems for the stimulation of biological activities within cells by applying electromagnetic stimulation to an electroactive material, wherein said electromagnetic stimulation is coupled to said electroactive material. In general, the present invention provides methods for the stimulation of biological activities within cells, which involves attaching or associating the desired cells to or with a surface comprising an electroactive material, and applying electromagnetic radiation directly to the desired area. In preferred embodiments, the stimulation of biological activities within cells results from inducing one or more activities including, but not limited to, gene expression, cell growth, cell differentiation, signal transduction, membrane permeability, cell division, and cell signaling. In exemplary embodiments, the electroactive materials are either two-dimensional substrates such as thin films having at least one surface of an electroactive material, or in alternative embodiments, the electroactive materials are three-dimensional substrates comprising a matrix, such as a polymer, and an electroactive material having at least one surface of an electroactive material.

Figure 2:
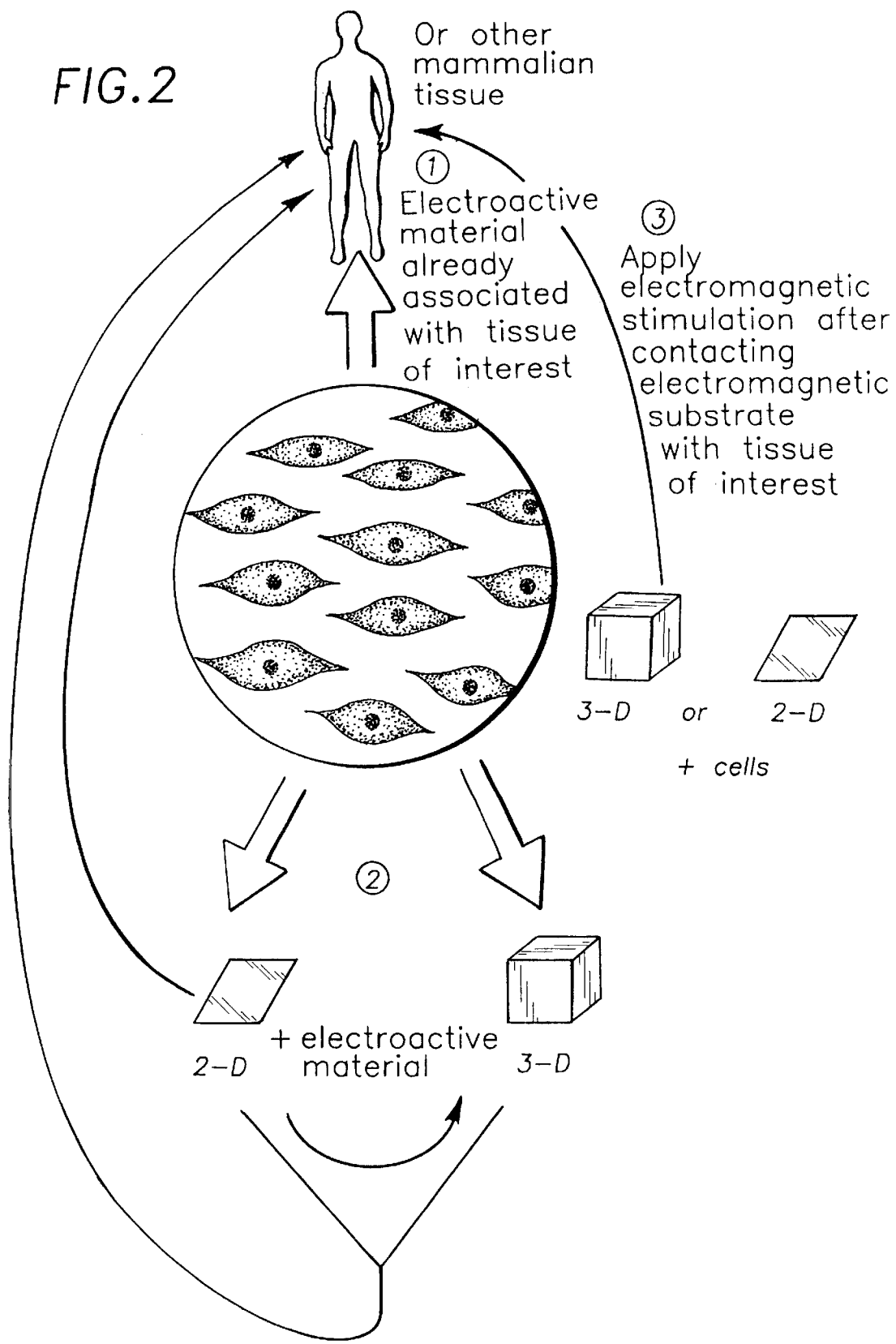
FIG. 2 depicts preferred embodiments for the method of the present invention.

As shown in FIG. 2, the inventive system can be applied using different methods. In one exemplary embodiment, as shown by the pathway labeled 1, cells are contacted with an electroactive substrate, which electroactive substrate already has attached thereto, or associated therewith, mammalian tissue, and subsequently applying electromagnetic radiation at the location of the electroactive substrate, the electromagnetic stimulation being coupled to the electromagnetic material. In another exemplary embodiment, as shown by the pathway labeled 2, a composition of cells and an electroactive substrate is first provided, which electroactive substrate has at least one surface of electroactive material, and wherein the cells are attached thereto or associated with the electroactive substrate. Subsequently, electromagnetic radiation is applied to the composition in vitro, wherein the electromagnetic stimulation is coupled to the electroactive material, and finally the composition is contacted with mammalian tissue to effect stimulation of cell function. In this particular embodiment, one of ordinary skill in the art will realize that, alternatively to contacting the composition including the cells and the electroactive substrate with the mammalian tissue, the cells can first be dissociated from the electroactive substrate after electromagnetic stimulation and then can be transferred to the tissue site of interest in the body (one or more mammalian cells). In yet another exemplary embodiment, as shown by the pathway labeled 3, a composition of cells and an electroactive substrate is first provided, wherein the electroactive substrate has at least one surface of electroactive material, and wherein the cells are attached thereto or associated with the electroactive substrate. Subsequently, the composition is then contacted with mammalian tissue, and finally the electromagnetic radiation is applied in vivo, wherein said electromagnetic stimulation is coupled to the electroactive material. In particularly preferred embodiments, the electromagnetic stimulation is coupled to the electroactive material by physical contact. In other embodiments, the electromagnetic stimulation is coupled to the electroactive material by electromagnetic induction.

In each of these embodiments, the electroactive materials for use in the present invention can be formulated as a two-dimensional substrate, for example, as a thin film of the substrate to which the desired cells are attached, or as a three-dimensional substrate, for example as a polymer coating on any three-dimensional matrix. Particularly preferred three-dimensional matrices include, but are not limited to polymers, biological polymers, and cellular solids, including, but not limited to, foam-like materials. The matrices used in the present invention are also preferably biodegradable.

Figure 3:
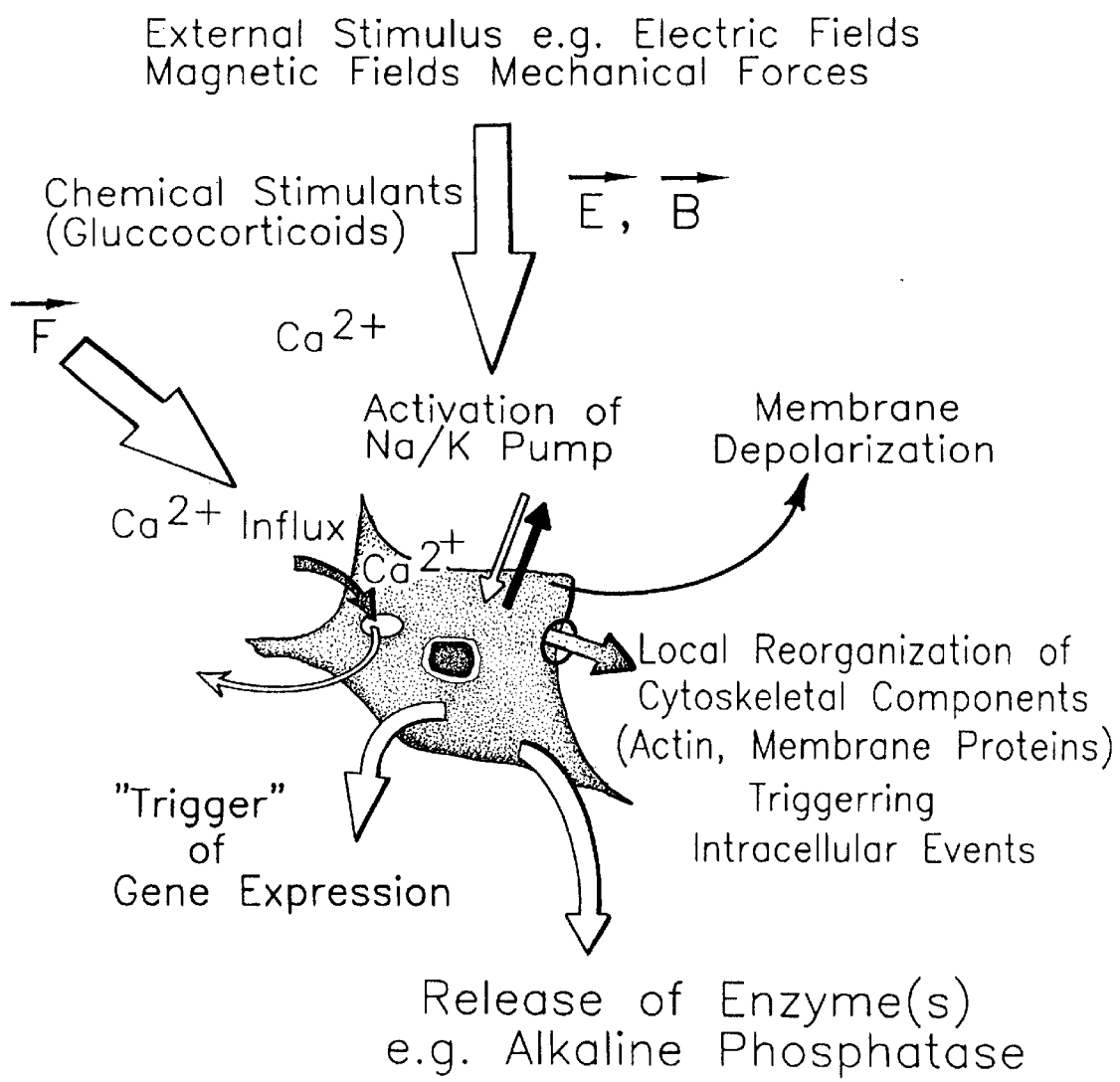
FIG. 3 depicts the effect of an external stimulus on cells.

Use of the inventive compositions, methods and systems enable the stimulation of one or more biological activities within cells by a variety of mechanisms (FIG. 3), such as, but not limited to, conformational changes in readsorbed proteins on the electroactive substrate upon electromagnetic stimulation, by electrophoretic redistribution of cytoskeletal components, by activation of voltage gated $Ca^{2+}$ and Na/K ion channels, and by depolarization of membrane resting potentials. In particular, each of these are capable of affecting such biological activities within the cell such as, gene expression, cell growth, cell differentiation, cell signal transduction, and cell signaling, to name a few.

In preferred embodiments, cells are preferably stem cells. A stem cell, for this invention, refers to any pluripotent cell that under the proper conditions will give rise to a more differentiated cell. Stem cells which may be used in accordance with the present invention include hematopoietic, neural, mesenchymal, gastrointestinal, hepatic, renal, muscle, cardiac muscle, kidney, skin, lung, bone marrow stromal cells, and embryonic stem cells. To give but one example, a hematopoietic stem cell can give rise to differentiated blood cells (i.e., red blood cell (erythrocyte), white blood cell (T-cell, B-cell, neutrophil, basophil, eosinophil, monocyte, macrophage, or platelet) or neural or muscle cells. Preferred cells for use in the present invention are further characterized in that they are capable of responding to electrical fields, they are easily isolable for in vitro and in vivo studies, and they are not substantially contaminated by other cell types. Stem cells can also be characterized by their ability (1) to be self-renewing and (2) to give rise to further differentiated cells. This has been referred to as the kinetic definition.

Figure 4:
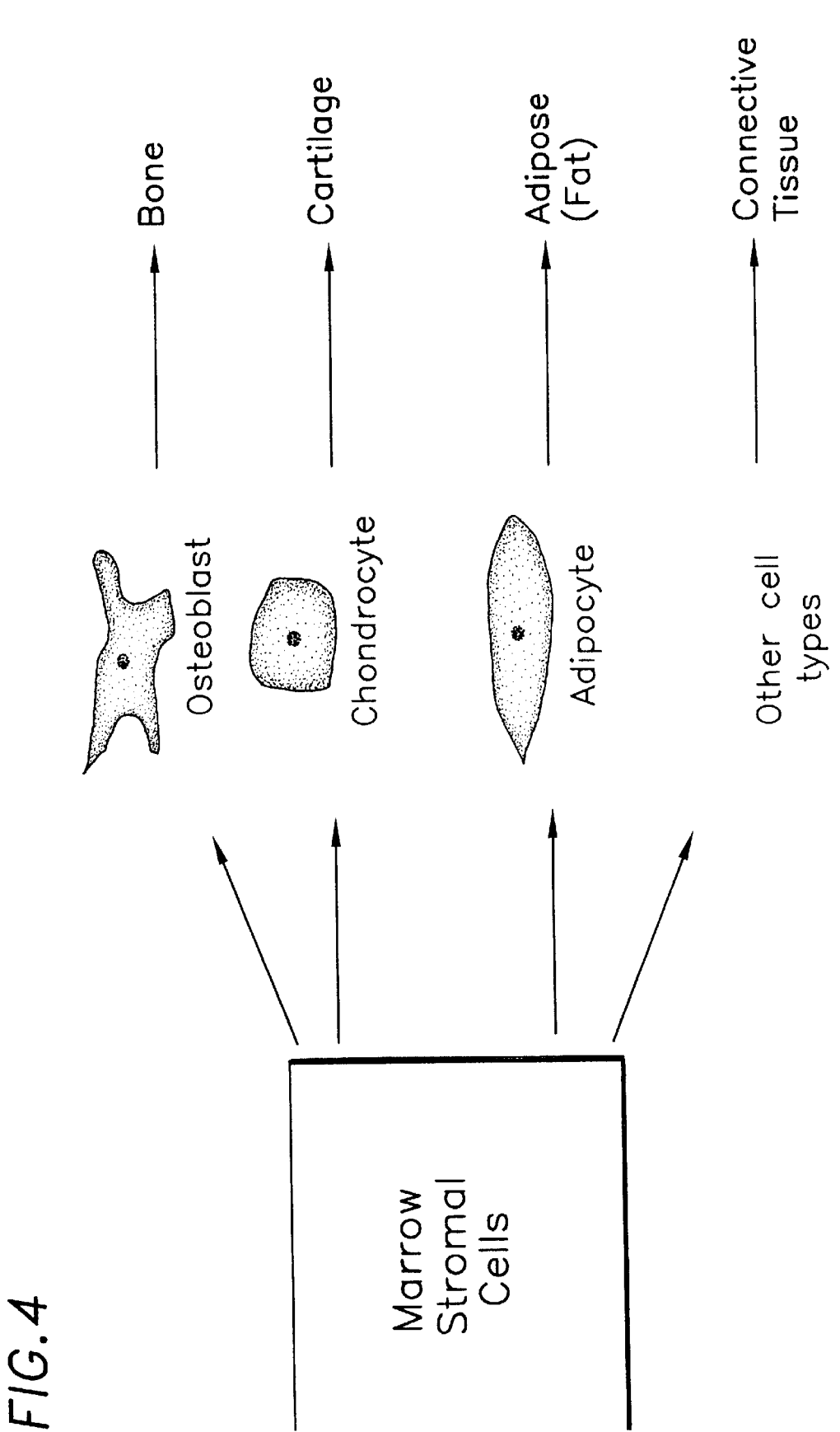
FIG. 4 illustrates a variety of end-stage phenotypes into which marrow stem cells may differentiate.

For the purposes of the present invention, stem cells are characterized in that they are not themselves terminally differentiated, they can divide without limit, and when they divide, each daughter cell has the choice of either remaining a stem cell or embarking on a course leading irreversibly to terminal differentiation. FIG. 4 shows that stem cells are capable of differentiating though a series of separate and unique lineage transitions into a variety of end-stage phenotypes. According to the current hypothesis, while a particular stem cell usually differentiates according to a specific pattern (e.g., neural stem cells into some type of nerve cell), exposure to appropriate growth factors or other environmental modification may cause differentiation into a wide variety of cells. For example, bone marrow stromal cells in vivo are pluripotent and are progenitor cells for a number of different cell lineages, including those of bone, cartilage, fat and fibrous tissues (FIG. 4).

As discussed previously, in the inventive method, the cells are applied to an electroactive material. This application can occur prior to contacting the electroactive material with mammalian tissue, or after contacting the electroactive material with mammalian tissue. Particularly preferred electroactive materials for use in the present invention include electroactive polymers. As discussed above, electroactive polymers are utilized in the present invention because of their ability to respond to electromagnetic stimuli. Based upon this ability, they can act as an interface between the external and physiological environments of a connective tissue, such as bone, which is capable of undergoing repair and regeneration on exposure to the same stimuli. In but one example, electroactive polymers are able to exploit the piezoelectric nature of bone and also act as interactive scaffolds for bone repair. In preferred embodiments the electroactive materials used in the present invention are also selected for their compatibility with the cells utilized.

In general, electroactive polymers comprise any polymer that contains a pocket of electron density and is capable of undergoing a phase transition upon subjecting the polymer to an electromagnetic field stimulus (See, for example, Shastri, V. R. and Pishko, M. V. "Biomedical Applications of Electroactive Polymers" in *Electrical and Optical Polymer Systems: Fundamentals, Methods and Applications,* Eds. D. L. Wise, D. J. Trantolo and G. E. Wnek, World Scientific Publishing Co., Chapter 30, 1031–1051 (1998)). Examples of specific electroactive polymers suitable for use in the present invention include, but are not limited to, conducting polymers, non-conducting polymers, piezoelectric polymers, semiconducting polymers, insulators, and substituted ionomer resins (ionons). The electroactive polymers of the present invention may be conductive, as for example, polypyrrole, or may alternatively be a polymer having a backbone substituted with electroactive moieties such as heme, porphyryn, or ferrocene. For example, ionomer resin, a copolymer of ethylene and a vinyl monomer with an acid group, contains positively and negatively charged groups suitable for substitution of other electroactive moieties. Other polymers that are conductive or that have regions of high electron density are suitable in the practice of the present invention and include, but are not limited to, poly (p-phenylene), poly(p-phenylene-vinylene), poly (thiophene), and poly(aniline). Another suitable polymer is hemosin, which is a polymer of heme, a component of hemoglobin. Other polymers particularly preferred for use in the present invention include intelligent polymers which include, but are not limited to gels, and polyacrylamide gels.

Particularly preferred electroactive polymers suitable for use in the present invention include conductive polymers. Interestingly, a key property of most polymers, which distinguishes them from metals, is their inability to conduct electricity. However, during the past 25 years, a new class of organic polymers has been devised with a remarkable ability to conduct electrical current. These electrically conducting polymers typically possess a conjugated backbone with a high degree of p-orbital overlap. Through a process known as "doping", the neutral polymer can be oxidized or reduced to become either positively charged (oxidative, p-type) or negatively charged (reductive, n-type). The generation and propagation of charge occurs via polarons or bipolarons along the oxidized polymer backbone. The conductive form of the polymer contains counterions that serve to maintain charge neutrality but do not affect the oxidation level of the polymer.

More particularly, the invention is described with reference to polypyrrole and its use in tissue engineering. This example is provided only for the purpose of illustration and is not intended to limit the scope of the present invention. As one of ordinary skill in the art will realize, the inventive compositions, methods and systems can be applied to a range of biological activities within cells and can employ a variety of electroactive materials to effect biological activities within cells.

Example: Use of Polypyrrole in the Present Invention

Figure 5:
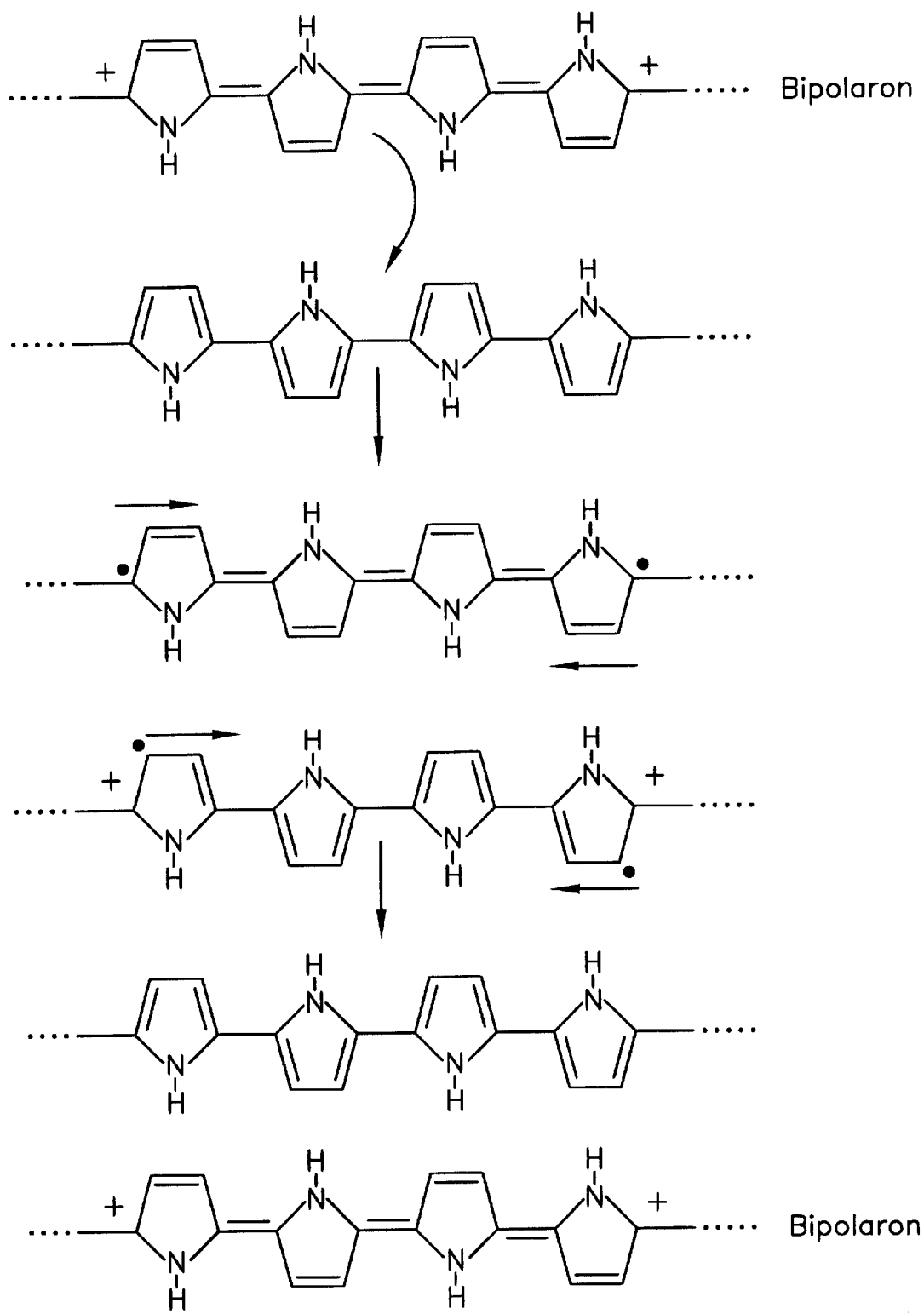
FIG. 5 depicts the mechanism of electronic conduction in oxidized polypyrrole (PPy) via interchain hopping of bipolarons. (Reproduced from Shastri, V. R., *Evaluation of polypyrrole thin films as substratum for mammalian cell culture.* Troy, N.Y.: Rensselaer Polytechnic Institute, 1995)

In an exemplary embodiment, polypyrrole is employed for use in the present invention, although one of ordinary skill in the art will realize that the following discussion can be applied to other abovementioned electroactive materials and electroactive polymers. Polypyrrole, which belongs to the class of aromatic poly(heterocyclics) has been extensively studied. It was first electrochemically synthesized by Diaz and co-workers (Diaz et al., *J. Chem. Soc. Chem. Commun.*, 1979, 635), and can be synthesized both by chemical and electrochemical means. Through the "doping" process, charge neutrality is maintained by incorporating dopant ions into the polymer backbone. FIG. 5 shows the mechanism by which the electronic conduction in polypyrrole occurs. The neutral polymer chain is oxidized with the removal of electrons to form radical cations. The radical ions are delocalized over a portion of the backbone, creating a structural defect known as a polaron, which contains both spin and positive charge. Two polarons can diffuse together and combine spins to form a bond, leaving a bipolaron species. The positive charges on the polymer backbone act as charge carriers for electrical conduction. Conduction can either occur along segments of the conjugated chain, or though charges hopping between chains.

Polypyrrole has been studied extensively due to its chemical and thermal stability, ease of preparation and electroactivity. It has been evaluated for a number of applications, such as amperometric glucose sensors (Couves, L. D., *Synth. Met.*, 1989, 28, C761), creatinine microbiosensors (Osaka et al., *J. Electrochem. Soc.*, 1998, 145, 406), immobilized enzyme-based analyte detection systems (Guiseppi-Elie et al., *Mater. Res. Soc. Symp. Proc.*, 1996, 413, 439) and electrodes to obtain electrochemically controlled dopamine release (Miller et al., *Macromolecules*, 1987, 20, 1594; Zhou et al., *J. Electroanal. Chem.*, 1989, 261, 147). Furthermore, its in vitro compatibility with mammalian cells has been explored (Shastri, V. R., Evaluation of polypyrrole thin films as substratum for mammalian cell culture, 1995 Rensselaer Polytechnic Institute: Troy, N.Y.; Wong et al., *Proc. Natl. Acad. Sci.*, 1994, 91, 3201). From these studies, it has been shown that both cell-surface interactions and cellular functions on polypyrrole thin films could be controlled by either changing the oxidation state of the polymer or by changing the wettability of the polymer through the use of suitable dopants. Since surface characteristics such as charge density and wettability play a key role in protein-adsorption and cell-biomaterial interactions (Tamada et al., "Cell Attachment to Various Polymer Surfaces", in Polymers in Medicine II: Biomedical and Pharmaceutical Applications, P. G. E. Chiellini, Migliaresi, C., Nicolais, L., Ed., 1986: New York, 101; Schakenraad et al., *J. Biomed. Mater. Res.*, 1986, 20, 773; Shastri et al., *Mater. Res. Soc. Symp. Proc.*, 1996, 414, 113), it is desirable to engineer a material such as polypyrrole, that allows flexibility in predicting cellular behavior.

The synthesis and characterization of polypyrrole is described in Example 1. The surface properties of the PPy thin films were characterized by XPS. The surface composition of the PPy films at a take-off angle of 35 is shown in Table 1 below.

TABLE 1

| Atom | % Composition |
| --- | --- |
| O 1s | 25.81 |
| Na (Auger) | 5.21 |
| N 1s | 6.26 |
| C 1s | 59.40 |
| S 2p | 3.31 |
| N/S | 1.89 |
| Na/S | 1.57 |

Figure 6:
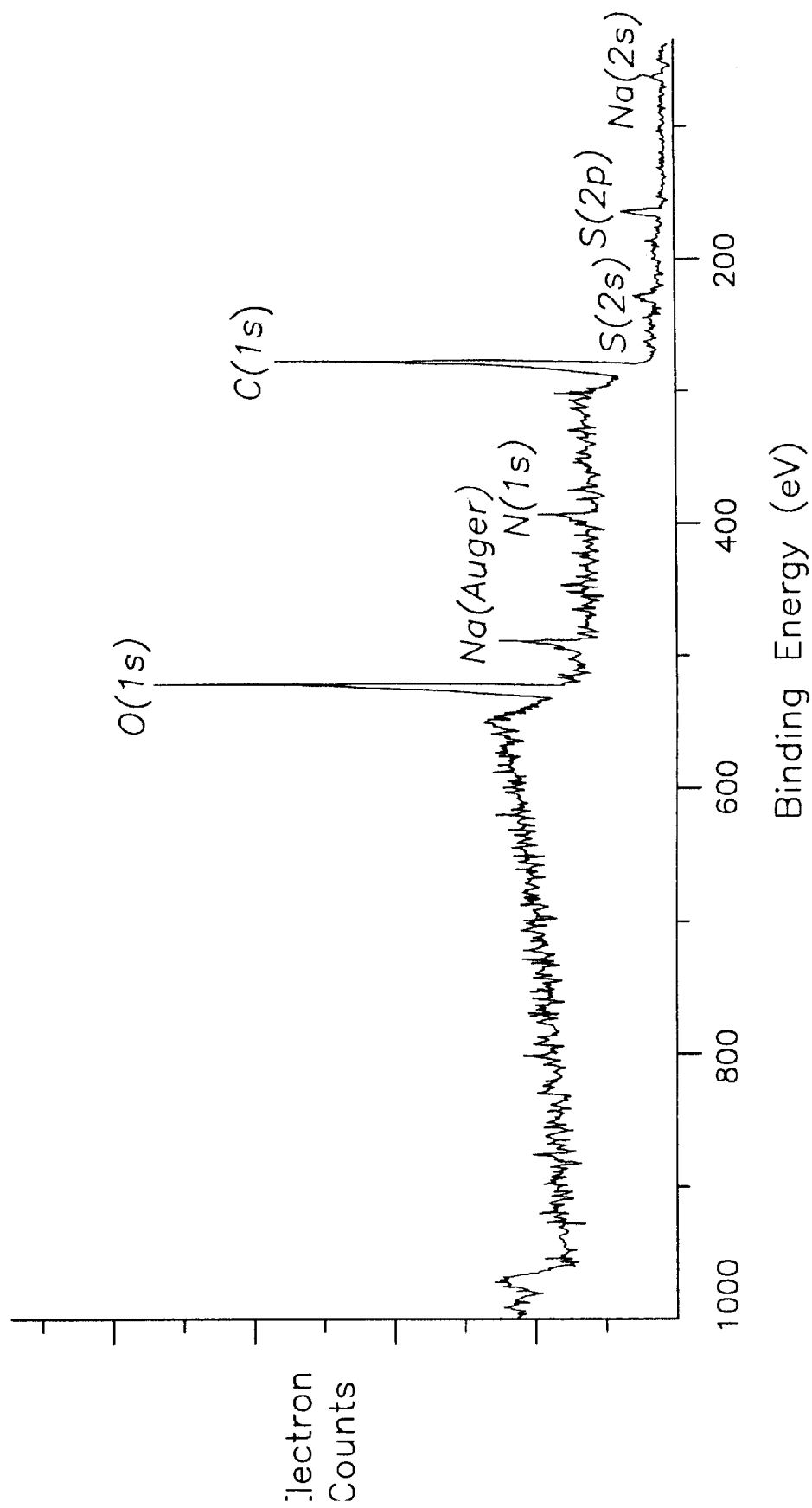
FIG. 6 depicts the XPS spectrum of PP-PSS thin film (0.1 $\mu$m thickness; x-ray spot size=1000 $\mu m^2$; electron flood gun energy=5 eV).

The corresponding XPS spectrum is shown in FIG. 6. The surface composition within a sampling depth of 10–100 Å indicates the presence of Na and S atoms from the sodium salt of poly(styrenesulfonate) (PSS) dopant. The surface N/S ratio was found to be consistent with results from comparable analysis depths (Beelen et al., *Synth. Met.*, 1991, 41 (Part I), 449; Neoh et al., *J. Phys. Chem. B*, 1997, 101, 726). That the surface is rich in negatively charged sulfonate groups is indicated by the presence of Na atoms, which are the associated cations with the pendant sulfonate group. The presence of the Na also indicates that the sulfonate groups are still in the salt form and were not protonated during the electrodeposition process. Furthermore, the almost 1:1 ratio of Na/S (1.57), demonstrates that the source of the Na is not merely a result of adsorbed ions in an electrical double layer, the layer formed at an electrolyte-electrode interface due to the interaction of ions in the electrolyte solution and charges in the electrode.

Figure 7:
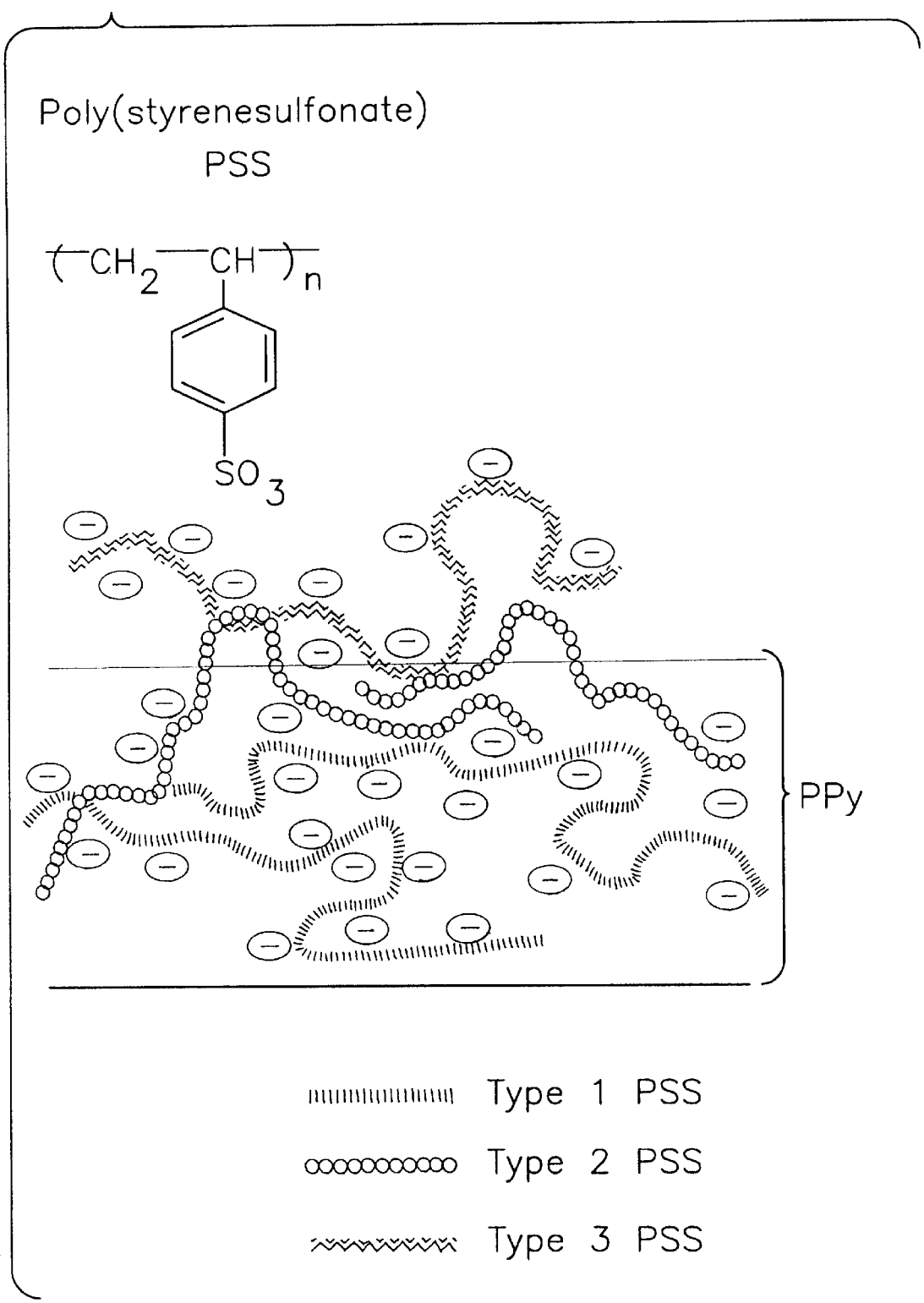
FIG. 7 depicts the proposed structure of PP-PSS films with three types of PSS chains. (Adapted from Prezyna, et al., *Macromolecules,* 24:5283–5287, 1991).

The presence of the negative sulfonate groups at the PPy/PSS surface is supported by previous work by Prezyna et al. (Prezyna et al., *Macromolecules*, 1991, 24, 5283). They suggested the presence of three types of PSS chains in the polypyrrole/PSS films (FIG. 7). The first (Type 1) includes well entangled chains contained in the bulk of the oxidized PPy film and are used relatively efficiently in doping. Type 2 PSS anions are thought to exist near the film surface, with only a portion of the chains acting as a dopant and the remainder are neutralized by Na cations in the electrolyte. Type 3 PSS chains are only slightly utilized as dopant chains and are loosely held by physical interactions at the film surface. It is the latter two types that have sulfonate moieties available for surface complexation and contribute to changing the nature of the polypyrrole/PSS surface. Thus, it can be concluded that the polypyrrole surface is rich in excess negatively charged sulfonate groups.

Figure 8:
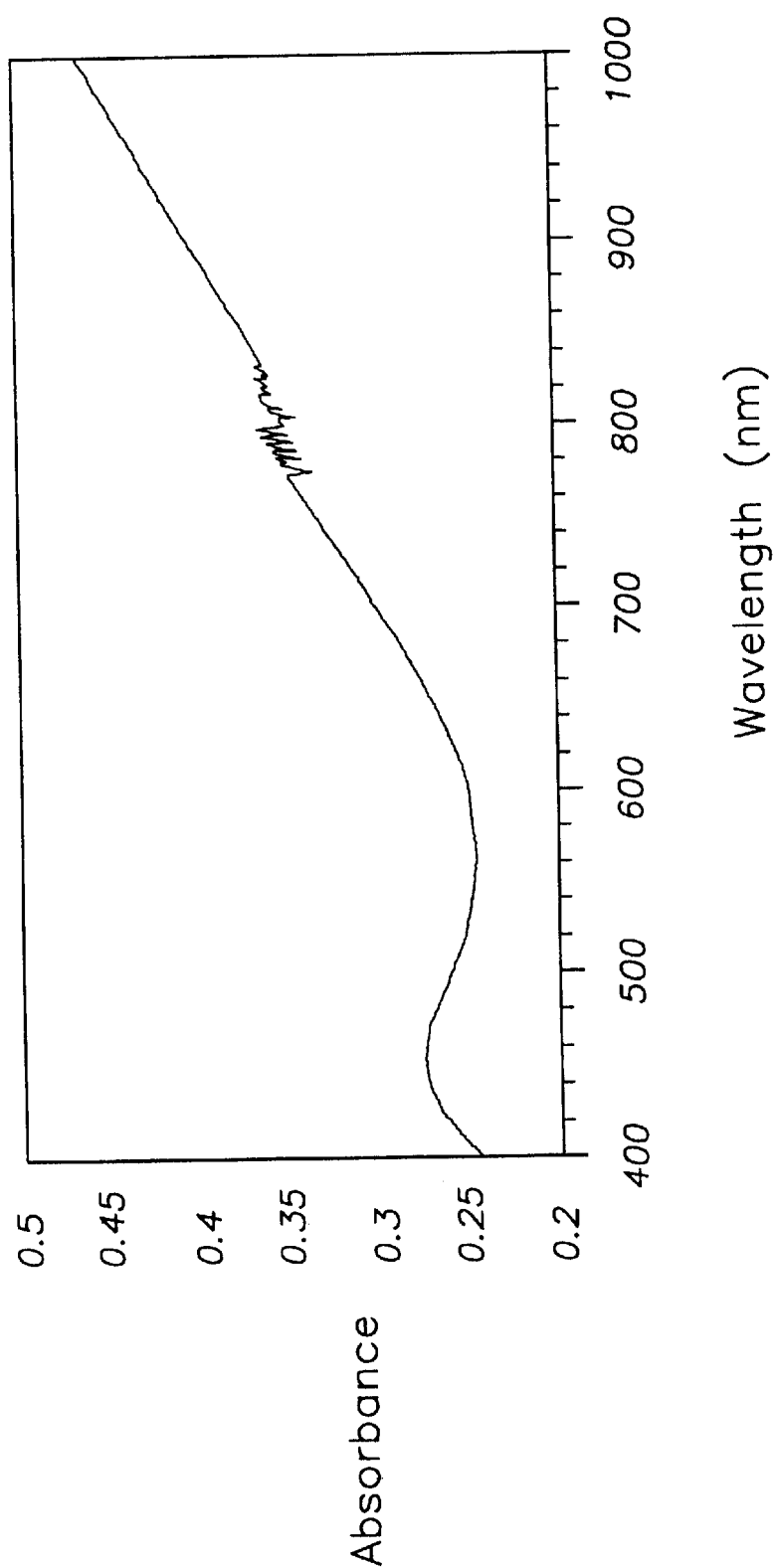
FIG. 8 depicts the UV/VIS absorption spectrum for 2PP-PSS 0.1 $\mu$m thick film.

The optical properties of PPy films were determined by UV/VIS spectroscopy (FIG. 8). The absorption spectrum shows a broad peak at 450 nm, which has been attributed to the oxidized polymer (Street, G. B., "Polypyrrole: From powders to plastics", in Handbook of Conducting Polymers, T. A. Skotheim, Ed., 1986: New York, 265). The broad peak around 800 nm is believed to be due to the presence of bipolarons in the oxidized polymer (Scott et al., *Synth. Met.*, 1984, 9, 165; Blackwood et al., *J. Phys. Chem.*, 1991, 95, 493).

SEM was used to analyze the surface and cross section of the PPy thin films. The thickness of the films, which was estimated by the amount of charge passed during the electrodeposition process, was 0.1 um. This thickness was found to correlate well with the observed thickness of 0.08–0.1 um, using SEM analysis of the cross section. At an accelerating voltage of 1 kV, the films were seen to have a rough morphology, with numerous nodules. Since a constant potential electrochemical method was used, the growth is by instantaneous nucleation followed by nodular growth on the initially nucleated sites. This leads to the observed rough morphology, which is consistent with previous studies in which polypyrrole was electrochemically synthesized at constant potential in aqueous media (Asavapiriyanont et al., *J. Electroanal. Chem.*, 1984, 117, 245; Ko et al., *J. Electrochem. Soc.*, 1990, 137, 905). Furthermore, the nodular structure of the PPy/PSS films were also observed by Yang et al. (Yang et al., *Langmuir*, 1991, 7, 556). They investigated the individual conformations of the PSS chains in the films by means of Scanning Tunneling Microscopy (STM). The PSS anions were found to be coated on the outside of the helical polypyrrole chains instead of being incorporated fully within the helical structure. This structural arrangement could be a further explanation for the presence of sulfonate moieties at the polypyrrole surface as observed by XPS, and also provide additional evidence for the model proposed by Prezyna (FIG. 7).

Additionally, the conductivity of the polypyrrole films was evaluated. Based on a rough estimate of the resistance, the conductivity was found to be in the order of 8.5 to 12 S/cm. The value confirmed that the polypyrrole was in the oxidized state. However, since thin films are being employed for the purposes of optically transparent substrates for cell culture studies, the conductivity is compromised. Conductivity in the order of 100 S/cm can be obtained with thicker films using the electrochemical synthesis method (Diaz et al., Bargon, J. "Electrochemical Synthesis of Conducting Polymers", in Handbook of Conducting Polymers, T. A. Skotheim, Ed., 1986: New York, 81).

The XPS results obtained suggest the presence of negatively charged sulfonate groups at the surface of the films. It is believed that these sulfonate moieties play a key role in the cellular interactions between the surface of the cells directly attached to it. SEM studies confirmed the rough nodular morphology of PPy films consistent with past observations. Conductivity and UV/VIS spectroscopy data established the existence of polypyrrole in its oxidized state.

After the polypyrrole is synthesized, it may be seeded with stem cells. The fate of the stem cells will be determined by their environment, including any voltage applied to the PPy and any regulatory factors added to the culture medium. For example, round neuronal cells produce dopamine. In the presence of nerve growth factor, these same cells will flatten, extend neurites, and decrease their dopamine production. However, the application of a voltage to the conductive polymer can also be used to stimulate a shape change in these cells.

The PPy need not be used alone. It may be coated with a molecular gel that is in turn seeded with cells. The gel will adhere to the PPy through hydrogen bonding interactions. Exemplary methods of producing such gels are described in U.S. Pat. No. 5,709,854, the contents of which are incorporated herein by reference. Because water is conductive, any voltage applied to the PPy will be conducted to the cells. Likewise, the PPy may be coated with poly(vinyl alcohol) (PVA). Cells seeded on the PVA may be stimulated to proceed from a differentiation phase to a mitotic phase by the application of an appropriate voltage.

The PPy may also be combined with other biocompatible polymers in a composite. Such polymers may also be biodegradable. Suitable biodegradable polymers are well known in the art and include collagen-GAG, collagen, fibrin, poly(lactic acid), poly(glycolic acid), and poly lactic-co-glycolic acid. In addition, biodegradable materials such as poly(anhydrides), poly(hydroxy acids), poly(ortho esters), poly(propylfumerates), poly(caprolactones), polyamides, polyamino acids, polyacetals, degradable polycyanoacrylates and polysaccharides may be combined with electroactive polymers as well. Non-biodegradable polymers appropriate for use in the invention include polystyrene, polyesters, polyurethanes, polyureas, poly(ethylene vinyl acetate), polypropylene, polymethacrylate, polyethylene, polycarbonates, and poly(ethylene oxide). Those skilled in the art will recognize that this is merely an exemplary list and that other biocompatible polymers exist that may be incorporated into the invention. These polymers may be combined with PPy to form a variety of composites. The composition of the composite may be optimized for the specific application. The polymers may be combined as interspersed layers or films or as fibers or blocks of one polymer inside a matrix of a second polymer. Either component of the composite may form a continuous or a discontinuous network. In addition, combinations of more than one type of polymer may be employed.

By seeding hematopoietic stem cells on the PPy, one can both enhance known biofunctions of the cells and direct the course of cell differentiation. A combination of selected growth factors and applied voltage may be used to stimulate a specific response. For example, hemangioblasts may be seeded on the PPy and cultured in the presence of vascular growth factor and a chemokine. When a voltage is applied, the cellular environment resembles a wound site, tricking the cells into behaving as if they were situated in distressed tissue and accelerating vascularization.

Constructs including PPy and stem cells may be used in both tissue healing and tissue regeneration applications. Use of stem cells in tissue engineering constructs for replacing diseased or damaged tissue bypasses the question of exactly what type of cells a matrix should be seeded with. Most tissues comprise a variety of cells (e.g.—neurites, astrocytes, Schwann cells, etc. in nervous tissue), and the concentration of the different types of cells may vary at different stages of development. By seeding a tissue engineering matrix with stem cells instead of fully differentiated cells, a practitioner need not determine the proper concentration of each type of cell. Instead, when the construct is implanted, the environment will trigger differentiation of the cells into the proper proportions for each cell type.

Tissue engineered constructs including stem cells may also be used to augment the function of existing tissue. For example, PPy matrices may be seeded with muscle stem cells and implanted to overlap paralyzed muscle tissue. The paralysis may result from nervous or muscular damage. The matrices will develop into contractile tissue that may be used to exercise the endogenous muscle and prevent atrophy. Such matrices may also be used as bioartificial pacemakers to stimulate (or replace) cardiac tissue. The contractile activity of the tissue is stimulated by applying a voltage across the PPy.

Experimentals

EXAMPLE 1

Polymer Synthesis and Characterization a. Chemicals and Materials: Pyrrole and sulfonated polystyrene sodium salt (MW 70,000) were obtained from Aldrich (Milwaukee, Wis.). Activated alumina was purchased from Mallinckrodt (Chesterfield, Mo.). Indium tin oxide (ITO) conductive borosilicate glass (40/square, 50×25 mm) was obtained from Delta Technologies (Still Water, Minn.) and used as the electrochemical conductive surface for PP film deposition. Hexane, dichloromethane and methanol were purchased from EM science (Gibbstown, N.J.). A platinum gauze (99.9% Pt, 52 mesh, woven from 0.1 mm diameter wire) served as the counter electrode and was purchased from Aldrich Chemical Co. An Ag/AgCl electrode was purchased from Fisher Scientific (Pittsburgh, Pa.) and was used as the reference electrode. Ultrapure water was obtained from Millipore Milli-Q Reagent Water System (Bedford, Mass.).

b. Polymer synthesis: Pyrrole was passed though an activated alumina column, consisting of a standard 9" pasteur pipette plugged with glass wool and packed with activated alumina, until it became colorless. Indium tin oxide substrates were ultrasonically cleaned in hexane, methanol and dichloromethane sequentially for 5 min. each. A three electrode setup was used for the electrochemical synthesis of polypyrrole (PPy): the ITO glass acted as the working electrode, the platinum mesh as the counter electrode and the Ag/AgCl electrode as the reference (FIG. 19). The electrodeposition solution contained 0.1 M pyrrole and 0.1 M sodium salt of poly(styrenesulfonate) (PSS) and Milli-Q ultra pure water. The sodium salt of poly(styrenesulfonate) served as both the electrolyte and dopant. An EG & G Princeton Applied Research Potentiostat/Galvanostat Model 253A (Princeton, N.J.) was employed as the constant voltage source. PPy films (0.1–0.15 um) were deposited onto the ITO glass at a constant potential of 0.7 V versus the Ag/AgCl reference electrode. The film thickness was controlled by the passage of charge: a charge of 26.2 $mC/cm^2$ yields a PPy film of 0.1 um in thickness.

c. X-Ray Photoelectron Spectroscopy (XPS) Spectra were obtained using a Surface Science Laboratories X-100 spectrometer (Mountain View, Calif.) employing a monochromatized Al Ka (1486.7 eV) Xray source operated under a source chamber vacuum of ~1×10-9 torr. Core level spectra were taken at a take-off angle of 35 (measured with respect to the normal to the sample surface). Photoelectrons were analyzed by a hemispherical multichannel detector in fixed analyzer transmission mode. An electron flood gun (energy 5 eV) was used to compensate for charging during X ray Photoelectron Spectroscopy data acquisition. A nickel mesh in electrical contact with the spectrometer was placed approximately 1 mm over samples to assist the compensation. For all spectra, the X-ray spot size was 1000 um. Survey spectra were recorded over a binding energy range of 0 to 1000 eV using a pass energy of 300 eV. Surface chemical compositions were determined from peak-area ratios corrected with the appropriate experimentally determined sensitivity factors.

d. UV/VIS Spectroscopy: UV/Visible spectroscopic data were obtained using a Cary SE UV-VIS-NIR Spectrophotometer from Varian OSI (Melbourne, Australia). A dual beam system with a scan rate of 600 nm/min was employed.

e. Scanning Electron Microscopy (SEM): A JEOL Scanning Microscope Model 6320 (Akishima, Japan) was used for surface and cross sectional analysis of the PPy thin films. PPy samples were mounted on aluminum stubs using conductive tape to observe the surface. For the cross section of the film, the PPy sample on the ITO glass was cut finely using a diamond cutter. It was mounted in a vice with the interface of interest facing up. Photographs of the images were obtained using a Polaroid instant camera and Polaroid 55 positive negative film.

f. Conductivity: Since the PPy films were grown on ITO (resistance of 40/sq reported by manufacturer), an estimate of the conductivity was made by measuring the resistance of the films with a Micronta multimeter. The probes of the multimeter were lightly touched onto the PPy film and the surface resistance was recorded. The surface conductivity, σ, the reciprocal of resistivity, ρ, was calculated from the cross-sectional, area (A) of the film and distance (L) between the multimeter probes as shown in equation X below:

$$\sigma = \left(\frac{1}{\rho}\right) = \left(\frac{L}{RA}\right)$$

What is claimed is:

1. A method for stimulating one or more biological activities within mesenchymal stem cells comprising:
    contacting tissue with an electroactive substrate, wherein said electroactive substrate has at least one surface of electroactive polymer, and wherein said electroactive polymer has attached thereto, or associated therewith, a matrix incorporating one or more mammalian mesenchymal stem cells; and
    applying electromagnetic stimulation at the location of the electroactive substrate, wherein said electromagnetic stimulation is coupled to said electroactive polymer.

2. The method of claim 1, wherein said stimulation of one or more biological activities results from an alteration in the cell membrane resting potential, wherein said electroactive substrate is capable of effecting the alteration in the cell membrane resting potential.

3. The method of claim 2, wherein said stimulation of one or more biological activities is selected from the group consisting of gene expression, cell growth, cell differentiation, cell death, cell signaling, cell signal transduction, cell contraction and any combination of these biological activities.

4. The method of claim 1, wherein said electromagnetic stimulation is coupled to said electroactive polymer by physical contact.

5. The method of claim 1, wherein said electromagnetic stimulation is coupled to said electroactive polymer by electromagnetic induction.

6. The method of claim 1, wherein said electroactive substrate is two-dimensional.

7. The method of claim 6, wherein said electroactive substrate comprises one or more thin films of said electroactive polymer.

8. The method of claim 1, wherein said electroactive substrate is three-dimensional.

9. The method of claim 8, wherein the electroactive substrate comprises an electroactive polymer associated with or attached to a matrix, wherein said matrix is selected from the group consisting of polymers, biological polymers, molecular gels, and cellular solids.

10. The method of claim 9, wherein the electroactive polymer is combined with the matrix to form a composite.

11. The method of claim 1, wherein said polymer is conductive.

12. The method of claim 1, wherein said polymer is a semiconductor.

13. The method of claim 1, wherein said polymer is an ionically conducting polymer.

14. The method of claim 1, wherein said electroactive polymer is selected from the group consisting of polypyrrole, poly(p-phenylene), poly(p-phenylene-vinylene), poly(thiophene), poly(aniline), poly(porphyryn), and poly(heme).

15. A tissue engineering method, comprising:
    providing a composition of mesenchymal stem cells and an electroactive substrate, wherein said electroactive substrate has at least one surface of electroactive polymer, and wherein said mesenchymal stem cells are attached thereto or associated with said electroactive substrate;
    applying electromagnetic stimulation to said composition, wherein said electromagnetic stimulation is coupled to said electroactive polymer; and
    contacting said composition with a mammalian tissue, wherein the step of contacting may be performed before or after the step of applying.

16. The method of claim 15, wherein said one or more biological activities is selected from the group consisting of gene expression, cell growth, cell differentiation, cell signal transduction, cell signaling, cell contraction and any combination of these biological activities.

17. The method of claim 15, wherein said electromagnetic stimulation is coupled to said electroactive polymer by physical contact.

18. The method of claim 15, wherein said electromagnetic stimulation is coupled to said electroactive polymer by electromagnetic induction.

19. The method of claim 15, wherein said electroactive substrate is two-dimensional.

20. The method of claim 19, wherein said electroactive substrate comprises one or more thin films of said electroactive polymer.

21. The method of claim 15, wherein said electroactive substrate is three-dimensional.

22. The method of wherein claim 21, wherein said electroactive substrate comprises an electroactive polymer associated with or attached to a matrix, wherein said matrix is selected from the group consisting of polymers, biological polymers, molecular gels and cellular solids.

23. The method of claim 22, wherein the electroactive polymer is combined with the matrix to form a composite.

24. The method of claim 15, wherein said polymer is conductive.

25. The method of claim 15, wherein said polymer is a semiconductor.

26. The method of claim 15, wherein said polymer is an ionically conducting polymer.

27. The method of claim 15, wherein said electroactive polymer is selected from the group consisting of polypyrrole, poly(p-phenylene), poly(p-phenylene-vinylene), poly(thiophene), poly(aniline), poly(porphyryn), and poly(heme).

28. A tissue engineering method, comprising:
providing a composition of mesenchymal stem cells and an electroactive substrate, wherein said electroactive substrate has at least one surface of electroactive polymer, and wherein said mesenchymal stem cells are attached thereto or associated with said electroactive substrate;
applying electromagnetic stimulation to said composition, wherein said electromagnetic stimulation is coupled to said electroactive polymer;
removing said stimulated cells from said electroactive polymer; and
contacting the stimulated cells with a mammalian tissue.

29. The method of claim 28, wherein said effecting the stimulation of one or more biological activities results from an alternation in the cell membrane resting potential, wherein said electroactive substrate is capable of effecting the alteration in the cell membrane resting potential.

30. The method of claim 28, wherein said one or more biological activities is selected from the group consisting of gene expression, cell growth, cell differentiation, cell signal transduction, cell signaling, cell contraction and any combination of these biological activities.

31. The method of claim 28, wherein said electromagnetic stimulation is coupled to said electroactive polymer by physical contact.

32. The method of claim 28, wherein said electromagnetic stimulation is coupled to said electroactive polymer by electromagnetic induction.

33. The method of claim 28, wherein said cells comprise.

34. The method of claim 28, wherein said electroactive substrate is two-dimensional.

35. The method of claim 34, wherein said substrate comprises one or more thin films of said electroactive polymer.

36. The method of claim 28, wherein said electroactive substrate is three-dimensional.

37. The method of claim 36, wherein said substrate comprises an electroactive polymer associated with or attached to a matrix, wherein said matrix is selected from the group consisting of polymers, biological polymers, molecular gels, and cellular solids.

38. The method of claim 37, wherein the electroactive polymer is combined with a matrix to form a composite.

39. The method of claim 28, wherein said polymer is conductive.

40. The method of claim 28, wherein said polymer is a semiconductor.

41. The method of claim 28, wherein said polymer is an ionically conducting polymer.

42. The method of claim 28, wherein said electroactive polymer is selected from the group consisting of polypyrrole, poly(p-phenylene), poly(p-phenylene-vinylene), poly(thiophene), poly(aniline), poly(porphyryn), and poly(heme).

43. A tissue engineering method, comprising:
providing a composition of mesenchymal stem cells and an electroactive substrate, wherein said electroactive substrate has at least one surface of electroactive polymer, and wherein said mesenchymal stem cells are attached thereto or associated with said electroactive substrate;
contacting said composition with a mammalian tissue; and
applying electromagnetic stimulation to said composition, wherein said electromagnetic stimulation is coupled to said electroactive polymer.

44. The method of claim 43, wherein said effecting the stimulation of one or more biological activities results from an alteration in the cell membrane resting potential, wherein said electroactive substrate is capable of effecting the alteration in the cell membrane resting potential.

45. The method of claim 44, wherein said one or more biological activities is selected from the group consisting of gene expression, cell growth, cell signal transduction, cell differentiation, cell signaling, cell death and any combination of these biological activities.

46. The method of claim 43, wherein said electromagnetic stimulation is coupled to said electroactive polymer by physical contact.

47. The method of claim 43, wherein said electromagnetic stimulation is coupled to said electroactive polymer by electromagnetic induction.

48. The method of claim 43, wherein said electroactive substrate is two-dimensional.

49. The method of claim 48, wherein said electroactive substrate comprises one or more thin films of said electroactive polymer.

50. The method of claim 43, wherein said electroactive substrate is three-dimensional.

51. The method of claim 50, wherein said substrate comprises an electroactive polymer associated with or attached to a matrix, wherein said matrix is selected from the group consisting of polymers, biological polymers, molecular gels and cellular solids.

52. The method of claim 51, wherein the electroactive polymer is combined with the matrix to form a composite.

53. The method of claim 43, wherein said polymer is conductive.

54. The method of claim 43, wherein said polymer is a semiconductor.

55. The method of claim 43, wherein said polymer is an ionically conducting polymer.

56. The method of claim 43, wherein said electroactive polymer is selected from the group consisting of polypyrrole, poly(p-phenylene), poly(p-phenylenevinylene), poly(thiophene), poly(aniline), poly(porphyryn), and poly(heme).

57. A system for stimulating one or more biological activities of cells comprising:
   a composition comprising an electroactive substrate, wherein said electroactive substrate has at least one surface of electroactive polymer, and wherein said electroactive polymer has attached thereto, or associated therewith, one or more mesenchymal stem cells; and
   an apparatus for applying electromagnetic energy at the desired location.

58. The system of claim 57, wherein said electroactive substrate is two-dimensional.

59. The system of claim 57, wherein said electroactive substrate is three-dimensional.

60. A two-dimensional stimulant of one or more biological activities comprising one or more films of an electroactive polymer, wherein said one or more films are associated with or attached to one or more mesenchymal stem cells.

61. A three-dimensional stimulant of one or more biological activities comprising an electroactive polymer associated with or attached to a matrix, and wherein said three-dimensional stimulant is associated with or attached to one or more mesenchymal stem cells.

* * * * *